(12) United States Patent
Bussemaker et al.

(10) Patent No.: US 8,219,323 B2
(45) Date of Patent: Jul. 10, 2012

(54) SYSTEM AND METHOD FOR QUANTIFYING THE SEQUENCE SPECIFICITY OF NUCLEOTIDE BINDING FACTORS

(75) Inventors: Harmen J. Bussemaker, New York, NY (US); Barrett C. Foat, St. Louis, MO (US); Ronald G. Tepper, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1282 days.

(21) Appl. No.: 11/803,777

(22) Filed: May 16, 2007

(65) Prior Publication Data

US 2008/0102460 A1 May 1, 2008

Related U.S. Application Data

(60) Provisional application No. 60/800,762, filed on May 16, 2006.

(51) Int. Cl.
*G01N 33/48* (2006.01)
*C12Q 1/68* (2006.01)
*G06F 7/60* (2006.01)
*G06G 7/58* (2006.01)

(52) U.S. Cl. .................... 702/19; 435/6; 702/20; 703/2; 703/11

(58) Field of Classification Search ........................ None
See application file for complete search history.

(56) References Cited

OTHER PUBLICATIONS

U.S. Appl. No. 12/569,794, filed May 16, 2007.
Zhu J, et al. (2008) "Integrating large-scale functional genomic data to dissect the complexity of yeast regulatory networks." Nat Genet. 40(7): 854-61.
Lee Si, et al. (2006) "Identifying regulatory mechanisms using individual variation reveals key role for chromatin modification." PNAS. 103(38): 14062-7.
Yvert G., et al. (2003) Trans-acting regulatory variation in *Saccharomyces cerevisiae* and the role of transcription factors. Nat Genet. 35(1):57-64.
Kim CG, et al. (2007) "Tamoxifen-induced activation of p21Wafl/Cip1 gene transcription is mediated by Early Growth Response-1 protein through the JNK and p38 MAP kinase/Elk-1 cascades in MDA-MB-361 breast carcinoma cells." Cell Signal. 19(6):1290-300.
Stormo, et al., "Quantitative analysis of the relationship between nucleotide sequence and functional activity." Nucleic Acids Res. Aug. 26, 1986;14(16):6661-79.
Schneider, et al., "Sequence logos: a new way to display consensus sequences." Nucleic Acids Res. Oct. 25, 1990;18(20):6097-100.
Bussemaker, et al., "Regulatory element detection using correlation with expression." Nat Genet. Feb. 2001;27(2):167-71.
Liu, et at, "Rationalization of gene regulation by a eukaryotic transcription factor: calculation of regulatory region occupancy from predicted binding affinities." J Mol Biol. Oct. 11, 2002;323(1):1-8.
Rovin, et al., "REDUCE: An online tool for inferring cis-regulatory elements and transcriptional module activities from microarray data." Nucleic Acids Res. Jul. 1, 2003;31(13):3487-90.
Djordjevic, et al., "A biophysical approach to transcription factor binding site discovery." Genome Res. Nov. 2003;13(11):2381-90.
Graneck, et al., "Explicit equilibrium modeling of transcription-factor binding and gene regulation." Genome Biol. 2005;6(10):R87. Epub Sep. 30, 2005.
Foat, et al., "Profiling condition-specific, genome-wide regulation of mRNA stability in yeast." Proc Natl Acad Sci U S A. Dec. 6, 2005;102(49):17675-80. Epub Nov. 29, 2005.
Tanay, A., "Extensive low-affinity transcriptional interactions in the yeast genome." Genome Res. Aug. 2006;16(8):962-72. Epub Jun. 29, 2006.
Foat, et al., "Statistical mechanical modeling of genome-wide transcription factor occupancy data by MatrixREDUCE." Bioinformatics. Jul. 15, 2006; 22(14):e141-9.

*Primary Examiner* — Shubo Zhou
(74) *Attorney, Agent, or Firm* — Baker Botts, L.L.P.

(57) ABSTRACT

Systems and methods for determining free energy parameters for predicting binding affinities of nucleotide sequences are provided. The disclosed subject matter obtains phenotypic measurements for nucleotide sequences (for example a DNA sequence or RNA sequence), links the phenotypic measurements to the nucleotide sequences to obtain linked pairs of phenotypic measurements and nucleotide sequences, estimates a relationship between the phenotypic measurements and the nucleotide sequences using the linked pairs, and obtains sequence specific affinity parameters from the estimated relationship.

13 Claims, 5 Drawing Sheets

SYSTEM AND METHOD FOR QUANTIFYING THE SEQUENCE SPECIFICITY OF NUCLEOTIDE BINDING FACTORS

CROSS REFERENCE TO RELATED APPLICATION

This application claims priority from U.S. Provisional Application Ser. No. 60/800,762, filed May 16, 2006, which is incorporated by reference herein.

STATEMENT REGARDING FEDERALLY SPONSORED RESEARCH

The disclosed subject matter described herein was funded in part by a grant from National Institutes of Health, grants GM008798, LM007276, GM63759, and HG003008. The United States Government may have certain rights hereunder.

BACKGROUND

The disclosed subject matter relates to a technique for quantifying the sequence specificity of nucleotide binding factors.

The sequence-specific regulatory activity of a nucleic acid binding trans-acting factor ("TF")—such as a DNA-binding protein, an RNA-binding protein, a non-coding RNA molecule such as a micro-RNA, or an RNA-protein complex, or a synthetic molecules such as a polyamide—is the result of energetically favorable interactions between amino acids exposed in the DNA binding domain of the TF and portions of nucleobases exposed in the major and/or minor groove of the DNA, or exposed by RNA. A computational method for discovering the sequence specificity of a TF cannot provide a quantitative description of TF binding unless it considers the physical underpinnings of the TF-DNA (or TF-RNA) interaction.

Current computational methods typically discover over-represented patterns in a set of nucleotide sequences considered to be bound by the TF. Such techniques use the information content of nucleotide patterns as a proxy for the free energy contributions of the bases found in the TF binding site. Other computational methods infer physically-based TF binding specificities from measured TF binding affinities for a small set of oligonucleotides or from structural modeling of protein-DNA interaction.

Genome-scale, quantitative measurements of TF occupancy are now available due to the advent of in vivo methods such as chromatin immunoprecipitation microarrays ("ChIP-chip") or DNA adenine methylase profiling ("DamID"), or in vitro methods such as protein binding microarrays ("PBM") and DNA immunoprecipitation microarrays ("DIP-ChIP"). Thus, it is no longer necessary to rely on small data sets, availability of protein-DNA structures, or the analogy between information content and statistical mechanics to infer free energy representations of transcription factor binding sites.

Unfortunately, the current techniques are limited in the ability to quantify the affinity of binding factors towards nucleotide sequences in a sequence specific manner. Such limitations arise from the inability to process large nucleotide sequences or inadequate structural modeling of the interactions between binding factors and nucleotide sequences. Accordingly, there exists a need for a technique for predicting binding affinities for nucleotide sequences.

SUMMARY

Systems and methods for determining affinity parameters for predicting binding affinities of nucleotide sequences are disclosed herein.

In an exemplary method, the disclosed subject matter obtains phenotypic measurements for nucleotide sequences, links the phenotypic measurements to the nucleotide sequences to obtain linked pairs of phenotypic measurements and nucleotide sequences, estimates a relationship between the phenotypic measurements and the nucleotide sequences using the linked pairs, and obtains sequence specific affinity parameters from the estimated relationship.

The phenotypic measurements can include chromatin-immunoprecipitation information, DNA-immunoprecipitation or protein binding microarray information, and absolute or differential messenger RNA expression information. The nucleotide-binding trans-acting factors can be DNA-binding proteins, RNA-binding proteins, non-coding RNA molecules such as micro-RNA's, RNA-protein complexes, or synthetic molecules such as polyamides. The physical parameters that quantify sequence specificity can be formatted into a matrix or graphical representation.

In some embodiments, interaction estimation can be accomplished using statistical mechanical modeling, or modeling including a model of interaction free energies between one or more binding factors and nucleotide sequences.

The disclosed subject matter also provides a system for determining affinity parameters for predicting binding affinities of nucleotide sequences. In some embodiments, the system includes an input device for receiving phenotypic measurements and nucleotide sequences, a processor to link the nucleotide sequences with the phenotypic measurements and to estimate a relationship between the nucleotide sequences and the phenotypic measurements, and a data store to store the obtained sequence specific affinity data from the estimated relationship.

The accompanying drawings, which are incorporated and constitute part of this disclosure, illustrate preferred embodiments of the disclosed subject matter and serve to explain its principles.

While the disclosed subject matter will now be described in detail with reference to the Figs., it is done so in connection with the illustrative embodiments.

DETAILED DESCRIPTION

Systems and methods for determining affinity parameters for predicting binding affinities of nucleotide sequences are disclosed herein. The disclosed subject matter obtains phenotypic measurements for nucleotide sequences (for example a DNA sequence or RNA sequence), links the phenotypic measurements to the nucleotide sequences to obtain linked pairs of phenotypic measurements and nucleotide sequences, estimates a relationship between the phenotypic measurements and the nucleotide sequences using the linked pairs, and obtains sequence specific affinity parameters from the estimated relationship.

Figure 1:
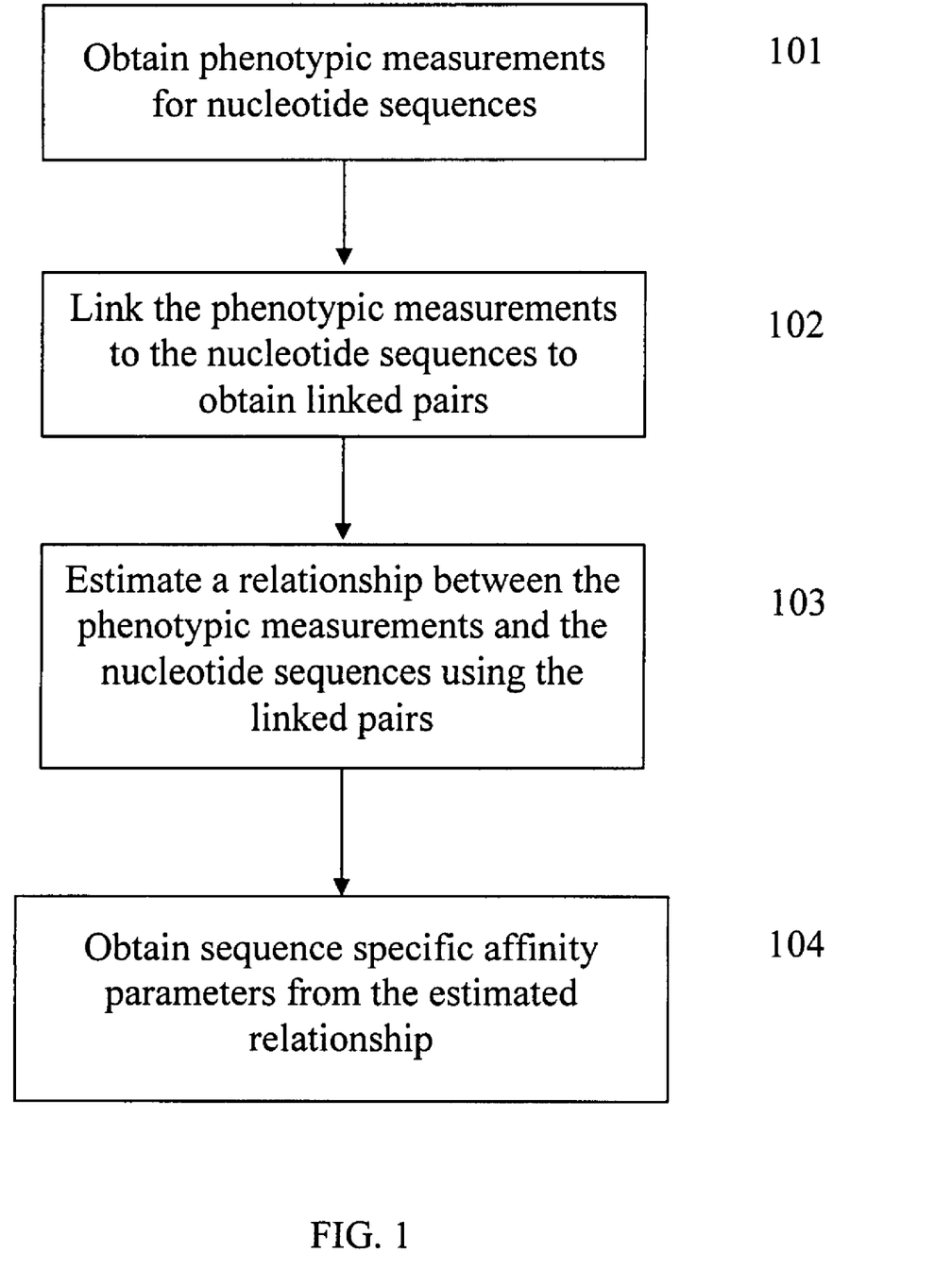
FIG. 1. is a diagram illustrating a method implemented in accordance with some embodiments of the disclosed subject matter.

FIG. 1 is a diagram illustrating a method implemented in accordance with some embodiments of the disclosed subject matter. One or more phenotypic measurements for the nucleotide sequences are obtained 101. The phenotypic measurements can include chromatin-immunoprecipitation information, DNA-immunoprecipitation or protein binding microarray information, absolute or differential messenger RNA expression information, or other information known by those skilled in the art.

One or more phenotypic measurements are linked to one or more nucleotide sequences to obtain two or more linked pairs the phenotypic measurements and the nucleotide sequences 102.

An estimation of the relationship between one or more phenotypic measurements and one or more nucleotide sequences using two or more linked pairs is performed 103. In some embodiments, the estimation includes a least-squares fit to a statistical-mechanical model of TF-DNA interactions, which will be further described below, to discover the relative contributions to the free energy of binding for each nucleotide at each position in the generalized TF binding site.

Sequence specific affinity parameters can be obtained 104 from an estimation process. The data can be represented as a position specific affinity matrix ("PSAM") containing the relative equilibrium constants of the TF-DNA interaction, with the highest affinity nucleotide at each position scaled to a value of one ($\Delta\Delta G=0$). The matrix can serve as the starting point to find the optimal PSAM.

The disclosed subject matter uses a minimization algorithm to determine the parameters of the PSAM. In order to compute a p-value that quantifies the statistical significance of the PSAM, it is necessary to have an appropriate null model.

In accordance with an aspect of the disclosed subject matter, a heuristic procedure can be used to obtain accurate p-values over a wide range of parameter values. The central quantity of interest is $|r|$: the absolute value of the Pearson correlation r between the predicted and measured values. The null distribution of $|r|$ can be determined empirically by executing repeated trials of disclosed subject matter on randomly generated sequence and measurement data.

Approximately 1000 trials were performed for each combination of parameters defining the sequence and measurement distributions. For each setting of these parameters, the distribution of $|r|$ was found to be well approximated by the Gaussian (normal) distribution. The mean of this normal distribution is dependent only on the number of sequence-measurement pairs (N), and the width (W) of the optimized PSAM (where W is the number of binding site positions optimized in the minimization step). In addition, the standard deviation of the empirical distribution of $|r|$ depends solely on the size of the data set (N).

The fact that the distribution of $|r|$ is almost entirely independent of the underlying distribution used to generate the randomized measurement data makes it possible to define a simple procedure for computing the p-value corresponding to $|r|$. The only dependence is on the parameters W and N; there is no dependence on the actual sequence and microarray data used.

The microarray data distributions sampled to reach this conclusion were the following: Gaussian (normal) distribution; skewed gaussian (all values greater than zero doubled); mixture of gaussians (90% with SD=1, 10% with SD=2); uniform (rectangular) distribution (an extreme case); permuted actual biological data (a realistic case).

The distribution of $|r|$ was also determined to be independent of the lengths of the sequences over a wide range, from ~200 to 2000 bases. Further, the distribution of $|r|$ does not depend on the overall base composition statistics of the sequence data, based upon trials using both randomized and true biological sequences.

Figure 2:
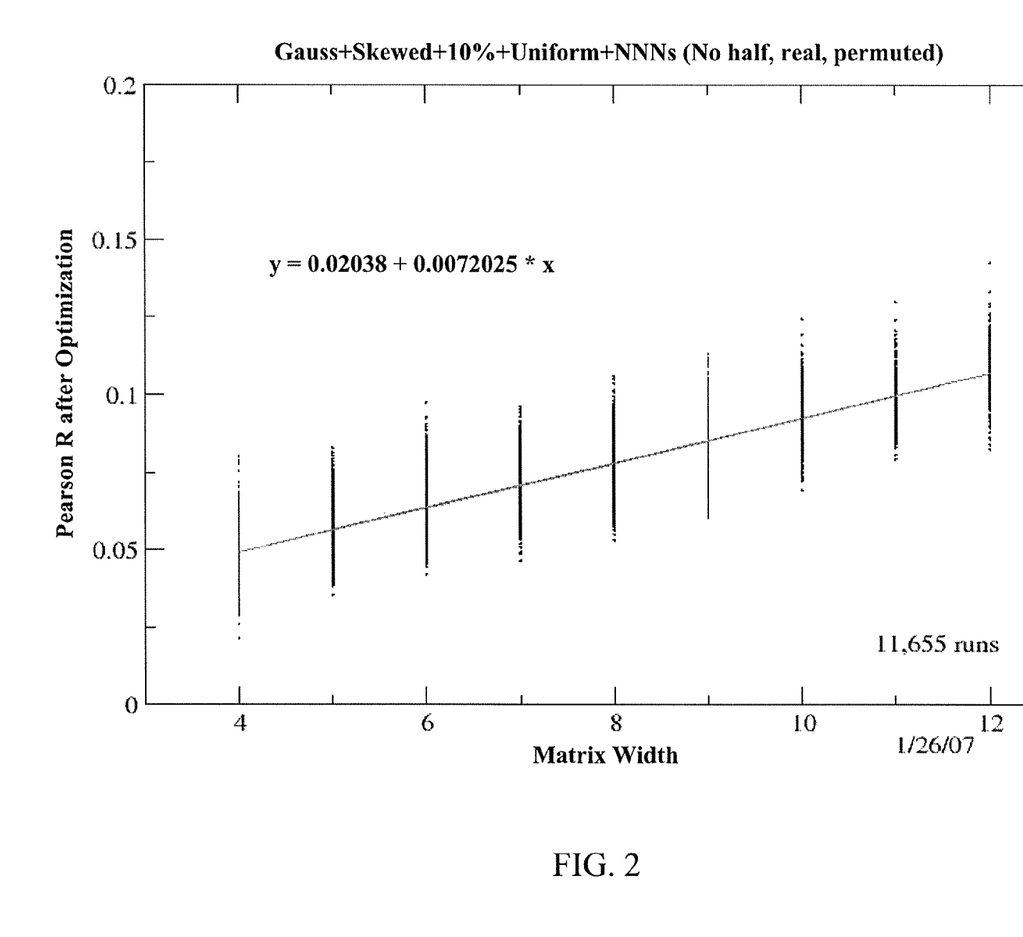
FIG. 2. is a chart plotting a distribution of optimized Pearson |r| values at various widths.

Referring next to FIG. 2, the result of the repeated trials at a range of effective PSAM widths W, with N=6505 sequences is shown. It can be seen that the mean of $|r|$ at each value of W (from 4 through 12) increases quite linearly with increasing W. Similar trials with smaller values of N demonstrated that the mean value of $|r|$ is inversely proportional to the square root of N.

From the above, the estimator of the mean of $|r|$ as a function of W and N under the null distribution is given by equation (1):

$$\mu_{|r|} = \frac{1.64 + 0.58 \times W}{\sqrt{N}} \quad (1)$$

The standard deviation of the distribution around this mean at each value of W is quite consistent and independent of W over the range, and it varies inversely as the square root of N. Specifically, the empirically estimated standard deviation is given by equation (2):

$$\sigma_{|r|} = \frac{0.66}{\sqrt{N}} \quad (2)$$

Using these results, a (pseudo-) z-score corresponding to the (signed) Pearson correlation r for an optimized PSAM of the disclosed subject matter can be determined as:

$$z_r = \frac{r - \left(\frac{r}{|r|}\right)\mu_{|r|}}{\sigma_{|r|}} \quad (3)$$

The corresponding p-value equals the area under the standard normal distribution at values $>|z_{|r|}|$.

The statistical-mechanical model used in some embodiments of the disclosed subject matter of 104 will next be described. Starting with a transcription factor P that binds to a DNA sequence S to form the TF-DNA complex PS:

$$P + S \underset{k_{off}}{\overset{k_{on}}{\rightleftharpoons}} PS \quad (4)$$

The affinity of the TF for the sequence can be expressed in terms of its equilibrium dissociation constant $K_d(S)$:

$$K_d(S) = \frac{[P][S]}{[PS]} = \frac{k_{off}}{k_{on}} = e^{\Delta G/RT}, \quad (5)$$

which is directly related to ΔG, the Gibbs free energy of binding per mole (R is the gas constant and T is temperature). The occupancy N(S) of sequence S by transcription factor P can be expressed as the concentration of TF-DNA complex divided by the total concentration of DNA (bound or unbound):

$$N(S) = \frac{[PS]}{[PS]+[S]} = \frac{[P]}{[P]+K_d(S)}. \quad (6)$$

For simplicity, it can be assumed that the TF concentration [P] is much smaller than $K_d(S)$. This assumption is physiologically plausible because in this regime, the highest affinity binding sites in the genome will be the most responsive to a change in the nuclear concentration of active TF. Thus, the occupancy becomes:

$$N(S) \approx \frac{[P]}{K_d(S)} = [P]K_a(S), \quad (7)$$

where $$K_a(S) \equiv K_d^{-1}(S). \quad (8)$$

Consider a single point mutation from the original reference sequence $S_{ref}$ to base b at position j resulting in the mutated sequence $S_{mut}$. Such a mutation will give rise to an additive change ΔΔG in the free energy of binding or, equivalently, a multiplicative change $w_{jb}$ in $K_a(S_{ref})$:

$$w_{jb} = \frac{K_a(S_{mut})}{K_a(S_{ref})} = e^{\Delta\Delta G/RT}, \quad (9)$$

where $$\Delta\Delta G = \Delta G(S_{ref}) - \Delta G(S_{mut}). \quad (10)$$

To be able to generalize the binding of transcription factor P to a sequence $S_{mut}$ with more than one point mutation, it can be assumed that the free energy contributions for each position in the binding site are independent and therefore additive. Equivalently, the $w_{jb}$'S for any nucleotide sequence can be multiplied to obtain the overall $K_a(S_{mut})K_a(S_{ref})$ ratio. Thus, the occupancy of a particular binding site $S_{mut}$ of length $L_w$ with nucleotide sequence $S_{mut}(1, 2, \ldots, L_w)=(b_1, b_2 \ldots, b_{L_w})$ is:

$$N(S_{mut}) = [P]K_a(S_{ref})\prod_{j=1}^{L_w} w_{jS_{mut}(j)}. \quad (11)$$

The occupancy $N(U_g)$ for the entire promoter region $U_g$, of gene g equals the sum of occupancies for each binding site window of length $L_w$ at each position i over the length $L_g$ of the sequence $U_g$:

$$N(U_g) = [P]K_a(S_{ref}) \sum_{i=1}^{L_g-L_w+1} \prod_{j=1}^{L_w} w_{jU_g(i+j-1)}, \quad (12)$$

where $U_g(i)$ is the base at position i in sequence $U_g$.

Recent innovations have provided indirect but quantitative information about the TF occupancy of large genomic regions. For each segment of DNA there are two microarray intensities. The test intensity $I_g^{test}$ is equal to a background intensity $\alpha^{test}$ plus a term that, to first approximation, is proportional (γ) to the occupancy $N(U_g)$ by the TF, either because the amount of TF bound to the probe contributes directly to the signal intensity (PBM) or because it determines the proportion at which an immunoprecipitated TF-DNA fragment is present in the sample (ChIP-chip or DIP-chip). The control intensity $I_g^{control}$ is only the result of background signal $\alpha^{control}$. Allowing for experimental noise Eg, Equation 13 is obtained:

$$\frac{I_g^{test}}{I_g^{control}} = \frac{\gamma N(U_g) + \alpha^{test}}{\alpha^{control}} + \epsilon_g \equiv \beta N(U_g) + C + \epsilon_g \quad (13)$$

Using Equation 9 for the occupancy $N(U_g)$, leads to Equation 11:

$$\frac{I_g^{test}}{I_g^{control}} = F \sum_{i=1}^{L_g-L_w+1} \prod_{j=1}^{L_w} w_{jU_g(i+j-1)} + C + \epsilon_g, \quad (14)$$

where $$F = \beta[P]K_a(S_{ref}). \quad (15)$$

Note that β, [P], and $K_a(S_{ref})$ cannot be determined separately without additional information such as the real protein concentration or $K_a(S_{ref})$.

The set of $w_{jb}$ elements as well as F and C can be calculated by performing a least squares to fit the measured intensity ratios:

$$(C, F, \{w_{jb}\}) = \underset{C,F,\{w_{jb}\}}{\operatorname{argmin}} \quad (16)$$

$$\sum_g \left( \frac{I_g^{test}}{I_g^{control}} - F \sum_{i=1}^{L_g-L_w+1} \prod_{j=1}^{L_w} w_{jU_g(i+j-1)} - C \right)^2.$$

The disclosed subject matter fits a quantitative model for how continuously valued genomic measurements should vary according to association of a nucleic acid binding factor with a substrate sequence that is associated with each measurement. This fit is done by using a numerical minimization procedure to find the least squared deviations between the nucleotide sequence-dependent model and the genomic measurements. The minimization procedure can use any of several algorithms to accomplish the task, including but not limited to the Levenberg-Marquardt algorithm, Broyden-Fletcher-Goldfarb-Shanno (BFGS) algorithm, Simplex algorithm of Nelder and Mead, Polak-Ribiere conjugate gradient algorithm, Fletcher-Reeves conjugate gradient algorithm, steepest descent algorithm, and Newton's method and variants.

The $4 \times L_w$ matrix of $K_a$ ratios $w_{jb}$ ($3L_w$. parameters plus $L_w$ reference nucleotide values) for all nucleotides at all positions in the binding site is referred to as the position specific affinity matrix (PSAM). Each position j in the PSAM is rescaled such that the largest $w_{jb}$ equal to unity, without loss of generality.

Differential mRNA expression microarray data, which measures the change in mRNA concentrations in cells from two different experimental conditions, can be used in place of genome-wide TF occupancy data. This substitution can be made since to first approximation, the transcription rate of genes is proportional to the total TF occupancy along the associated promoter regions. Genome-wide occupancy data can be preferable, however, since it is a more direct measure of TF-DNA interaction, and since the design of the experiments provides the TF identities for the discovered PSAMs.

Information content-based weight matrices are usually displayed as sequence logos. However, in accordance with some embodiments of the disclosed subject matter weight matrices can be discovered without a background sequence model. Thus, an appropriate logo can display the actual relative free energies of binding for each nucleotide at each position rather than information content.

Figure 3:
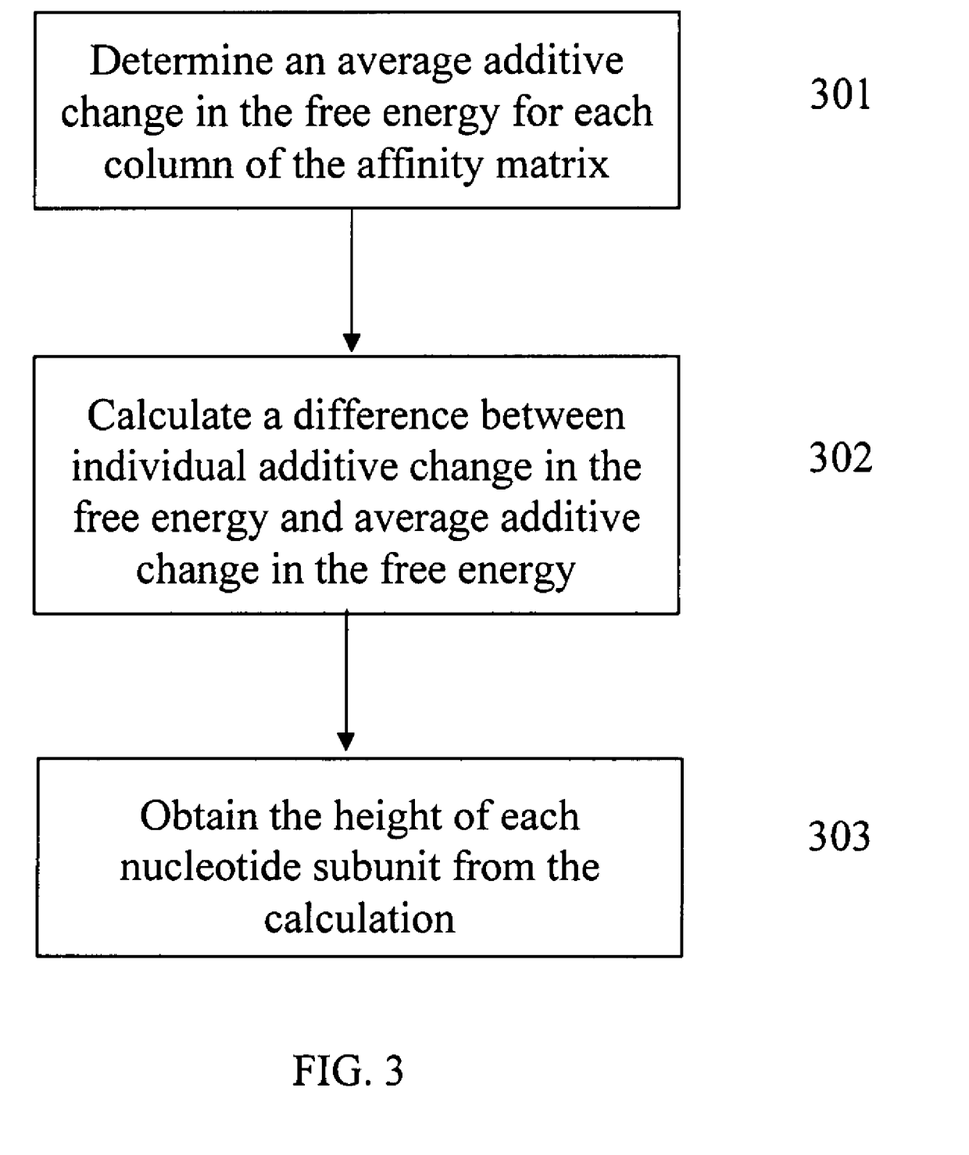
FIG. 3 is a diagram illustrating the construction of affinity logos in accordance with some embodiments of the disclosed subject matter.

Referring next to FIG. 3, the construction of affinity logos will be described as follows: For each position in the PSAM, the average $\Delta\Delta G$ is calculated 301. Then, the difference between each individual $\Delta\Delta G$ and the average $\Delta\Delta G$ at that position is computed 302; the absolute value of this difference is the height of the character representing that nucleotide 303. If the difference is positive (more favorable than average), the letter is placed above a horizontal black line through the center of the logo. If the difference is negative (less favorable than average) the letter is placed below the black line. Larger letters are stacked on smaller letters moving outward from the black line. The height of the letter can be interpreted as free energy difference from the average in units of RT.

Thus, an intuitive high amplitude is given to the nucleotide positions that most contribute to the sequence specificity of the TF. To highlight that the characters representing the high affinity nucleotides are above the black line, the characters representing the low affinity nucleotides are made partially transparent. However, maintaining the representation of the poor affinity nucleotides below the center line allows the viewer to immediately see which nucleotide substitutions are most unfavorable to binding.

Figure 4:
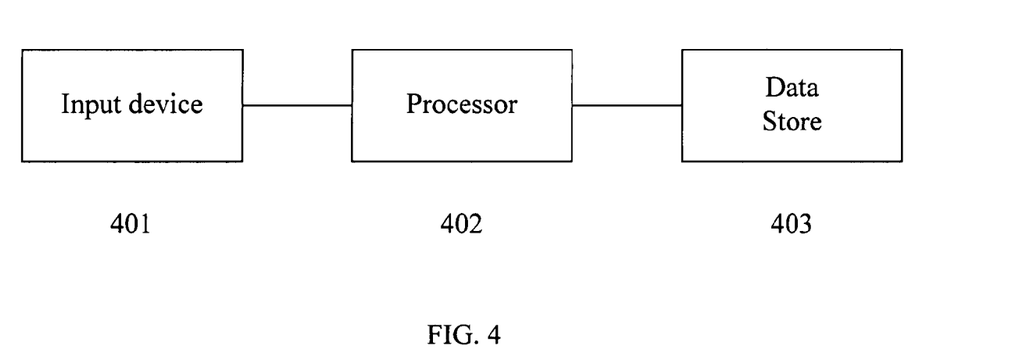
FIG. 4 is a block diagram of system in accordance with some embodiments of the disclosed subject matter.

FIG. 4 is a block diagram of system in accordance with some embodiments of the disclosed subject matter. In a preferred embodiment an input device 401 is used to receive phenotypic measurements and more nucleotide sequences. A processor 402 coupled to the input device runs appropriate software to link the phenotypic measurements and nucleotide sequences to obtain two or more linked pairs of phenotypic measurements and nucleotide sequences. Processor 402 also runs software to implement the procedure described above to estimate a relationship between the phenotypic measurements and nucleotide sequences using the linked pairs, and to obtain sequence specific affinity parameters from the estimated relationship.

A data store 403 receives sequence specific affinity data (Flow processor 402) and stores the obtained sequence specific affinity data from the estimated interactions. The data store can be implemented as RAM or any other memory device.

A monitor (not shown) or any display device can be used to display the sequence specific affinity data.

The processor can be implemented as a computer microchip, a stand alone computer or collection of networks computing or any device suitable for processing. The disclosed subject matter can be implemented in Perl, C, or other suitable programming language.

EXAMPLES

For all examples, the length of each of the two dyads of the seed motifs was three, the length of the added flanks on each side of the dyad was three, the minimum gap was zero, the k cross-validations were two, and $w_{min}$ was $10^{-5}$. For all runs on ChIP-chip and PBM data, the maximum acceptable P-value was $10^{-3}$ and the maximum dyad gap was twenty. For all runs on DIP-chip data, the maximum acceptable P-value was $10^{-6}$ and the maximum dyad gap was ten. For all runs on differential mRNA expression data, the maximum acceptable P-value was $10^{-3}$ and the maximum dyad gap was eleven.

In the example, microarray data was gathered from publication supplements. Specific TFs were analyzed based on the availability of experimental $K_d$ data or crystal structure data. PSAMs were inferred by the disclosed subject matter for chromatin immunoprecipitation microarrays (ChIP-chip) using the microarray data and microarray feature sequences from Harbison, et al. "Transcriptional regulatory code of a eukaryotic genome." Nature, 431, 99-104 (2004). These ChIP-chip experiments were performed under a variety of culture conditions, including rich media (YPD); sulfometuron methyl (SM), an inhibitor of amino acid biosynthesis; and treatment with rapamycin (RAPA). PSAMs were inferred for PBM experiments using the microarray data from Mukherjee, S., et al, "Rapid analysis of the DNA-binding specificities of transcription factors with DNA microarrays," Nat. Genet., 36, 1331-1339 (2004), and the feature sequence data from Harbison et al. as the two studies used the same array features. PSAMs were inferred for Leu3 using the DIP-chip microarray data and feature sequences from Liu, X., et al, "DIP-chip: rapid and accurate determination of DNA-binding specificity, " Genome Res. 15, 421-427 (2005). Liu et al. performed DIP-chip experiments using two different concentrations of Leu3, 4 nM and 40 nM, and PSAMs were inferred for each concentration. The PSAM for Ndt80 was inferred from differential mRNA expression microarray data measuring the sporulation response in a ndt80 deletion strain versus a wild-type strain as described in Chu, et al., "The transcriptional program of sporulation in budding yeast," Science, 282, 699-705 (1998), the contents of which are incorporated herein by reference. The sequence data for the Ndt80 PSAM inference was the 800 bp upstream of every yeast gene, retrieved from the Saccharomyces Genome Database described for example in (Issel-Tarver, et al., "Saccharomyces Genome Database, Methods Enzymol.," 350, 329-346 (2005), the contents of which are incorporated herein by reference, and purged of redundant sequences as described in Foat, B. C., et al. "Profiling condition-specific, genome-wide regulation of mRNA stability in yeast," Proc. Natl. Acad. Sci. USA, 102, 17675-17680 (2005), the contents of which are incorporated herein by reference. Microarray intensities were analyzed as the ratio of the experimental sample intensity to the control sample intensity with the exception of the ndt80 deletion data, which was analyzed as the $\log_2$-ratio. All microarray data was purged of extreme outliers before being analyzed.

The electrophoretic mobility shift assay (EMSA) is able to provide direct estimates of $K_d$'s for a TF binding to particular oligonucleotides. The ratio of the EMSA-measured $K_d$ of a reference oligonucleotide $S_{ref}$ to the $K_d$ of one of the other tested oligonucleotides $S_{mut}$ provides the same information as the product across the PSAM over the same sequence for the same TF. In the simplifying scenario where the length of the oligonucleotides is the same as the length $L_w$ of the PSAM, $$\frac{K_d(S_{ref})}{K_d(S_{mut})} = \prod_{j=1}^{L_w} w_j s_{mut(j)}. \quad (17)$$

While the biological processes involved are considerably more complex, lacZ expression data can be employed to the same end. If it is assumed that β-galactosidase activity, concentration of β-galactosidase, the amount of mRNA expressed, the specific recruitment of RNA polymerase to the promoter, and the promoter occupancy by the TF are all proportional to each other, then relative $K_d$'s are reflected in the ratio of β-galactosidase activities between the assay using the reference binding site and another assay using a different binding site. Thus, the lacZ reporter expression assay data can be used in a similar manner to EMSA-derived $K_d$ data to confirm the results of the disclosed subject matter.

Experimentally determined in vitro binding affinities and lacZ reporter expression activity data can be obtained from available publications. The $K_d$ data and lacZ expression data for Abf1 were attained from Gailus-Dumer, et al., "Participation of the yeast activator Abf1 in meiosis-specific expression of the HOP1 gene," *Mol. Cell. Biol.*, 16, 2777-2786 (1991); $K_d$ data for Leu3 from Liu, X. et al., "Rationalization of gene regulation by a eukaryotic transcription factor: calculation of regulatory region occupancy from predicted binding affinities" *J. Mol. Biol.*, 323, 1-8 (2002); and $K_d$ data and lacZ expression data for Ndt80 and Sum1 from Pierce, M., et al. "Sum1 and Ndt80 proteins compete for binding to middle sporulation element sequences that control meiotic gene expression," *Mol. Cell. Biol.*, 23, 4814-4825 (2003), the contents of which are incorporated herein by reference.

To compare the experimental $K_d$ measurements with PSAMs of the disclosed subject matter, all experimental $K_d$ and lacZ expression data was first converted to $K_a$ ratios by normalizing with respect to the value of the highest affinity oligonucleotide. The $K_a$ ratios were then log-transformed to obtain the ΔΔG values, PSAMs for each TF were converted to ΔΔG's relative to the highest affinity oligonucleotide from the respective experiment. The sum of the ΔΔG values was calculated for the best PSAM-matching window in each of the experimentally tested sequences. If a sequence was shorter than the PSAM, the sum was taken over only the best matching positions within the PSAM.

Figure 5:
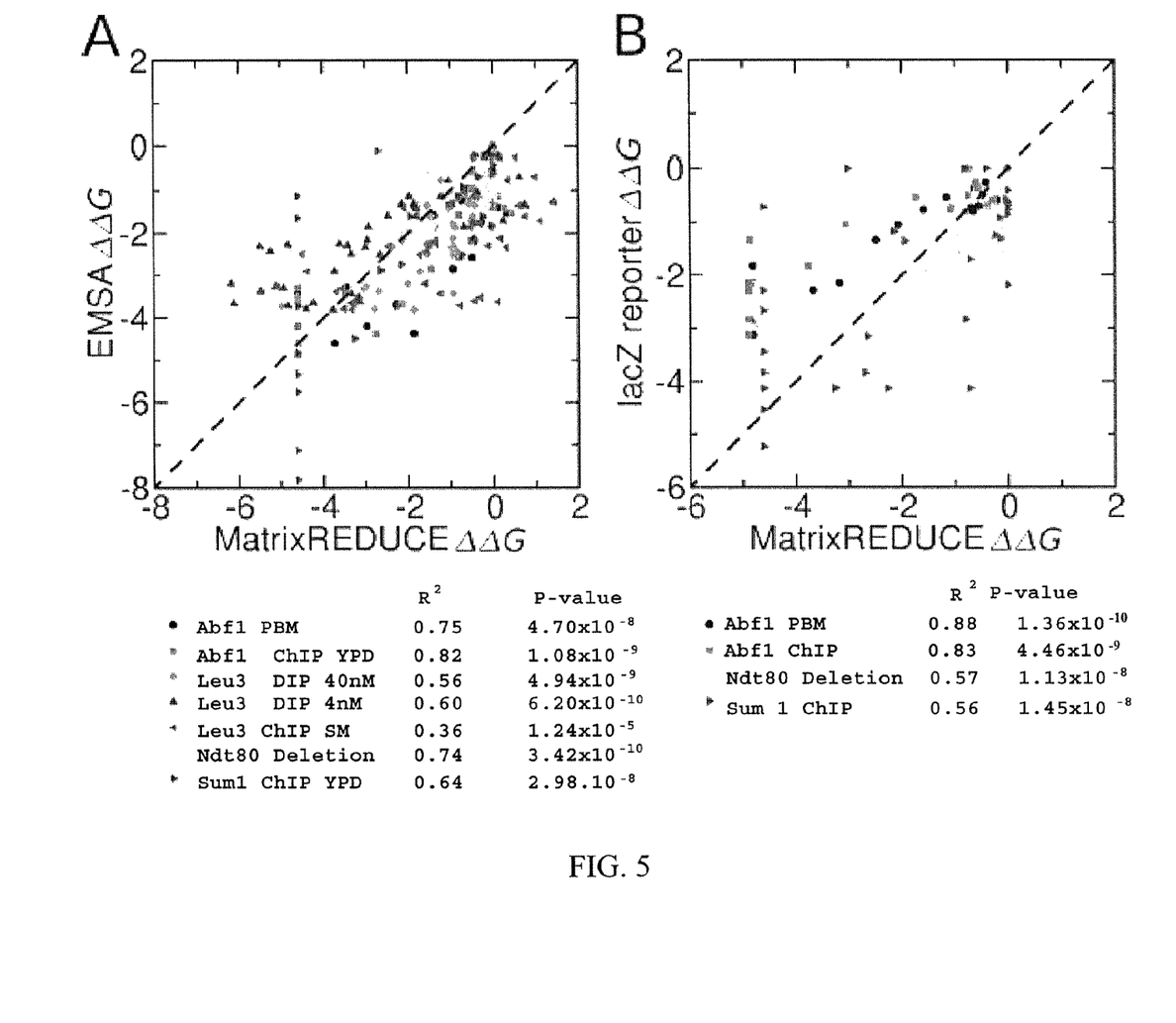
FIG. 5 is a chart comparing experimental $\Delta\Delta G$'s to PSAM $\Delta\Delta G$'s of an embodiment of the disclosed in the subject matter by plotting and by calculating Pearson correlations.

As shown in FIGS. 5A and B, experimental ΔΔG's were then compared to the PSAM ΔΔG's by plotting, and the degree of accordance between both methods was shown by calculating Pearson correlations.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention.

What is claimed is:

1. A method of determining one or more affinity parameters for predicting binding affinities of two or more nucleotide sequences each defined by unique nucleotide sequence information, comprising:
   (a) receiving two or more phenotypic measurements for said two or more nucleotide sequences;
   (b) linking, using a processor, said two or more phenotypic measurements to said two or more nucleotide sequences to obtain two or more linked pairs of said phenotypic measurements and said nucleotide sequences;
   (c) estimating a relationship between said two or more phenotypic measurements and said two or more nucleotide sequences using said two or more linked pairs; and
   (d) obtaining sequence specific affinity parameters from said estimated relationship.

2. The method of claim 1, wherein said phenotypic measurements are selected from the group consisting of chromatin immunoprecipitation information, protein binding microarray information, DNA immunoprecipitation information, and differential messenger RNA information.

3. The method of claim 1, further comprising formatting said sequence specific affinity parameters into a graphical representation.

4. The method of claim 1, wherein said two or more nucleotide sequences comprises DNA sequences.

5. The method of claim 1, wherein said two or more nucleotide sequences comprises RNA sequences.

6. The method of claim 1, wherein said estimating a relationship comprises statistical mechanical modeling.

7. The method of claim 6, wherein said statistical mechanical modeling comprises a model of free energy interactions between said two or more binding factors and said two or more nucleotide sequences.

8. The method of claim 7, wherein said two or more binding factors are selected from the group consisting of binding proteins, transcription factors, transacting factors, micro RNA, and synthetic molecules.

9. Apparatus for determining one or more affinity parameters for predicting binding affinities of two or more nucleotide sequences each defined by unique nucleotide sequence information, comprising:
   (a) an input device for receiving two or more phenotypic measurements and two or more nucleotide sequences;
   (b) a processor, coupled to said input device and receiving said two or more phenotypic measurements and said two or more nucleotide sequences therefrom, to link said two or more phenotypic measurements and said two or more nucleotide sequences to obtain two or more linked pairs of phenotypic measurements and nucleotide sequences; to estimate a relationship between said two or more phenotypic measurements and said two or more nucleotide sequences using said two or more linked pairs; and to obtain sequence specific affinity parameters from said estimated relationship; and
   (c) a data store, coupled to said processor and receiving said sequence specific affinity parameters therefrom, for storing said sequence specific affinity data.

10. The apparatus of claim 9, wherein said phenotypic measurements are selected from the group consisting of chromatin immunoprecipitation information, protein binding microarray information, DNA immunoprecipitation information, and differential messenger RNA information.

11. The apparatus of claim 9, wherein said two or more nucleotide sequences comprises DNA sequences.

12. The apparatus of claim 9, wherein said two or more nucleotide sequences comprises RNA sequences.

13. The apparatus of claim 9, wherein said estimating a relationship comprises statistical mechanical modeling.

* * * * *

UNITED STATES PATENT AND TRADEMARK OFFICE
CERTIFICATE OF CORRECTION

PATENT NO. : 8,219,323 B2 Page 1 of 1
APPLICATION NO. : 11/803777
DATED : July 10, 2012
INVENTOR(S) : Harmen J. Bussemaker, Barrett C. Foat and Ronald G. Tepper It is certified that error appears in the above-identified patent and that said Letters Patent is hereby corrected as shown below:

At column 10, line 3:

"(b) linking, using a processor, said two or more phenotypic" should read (b) linking, using a computer processor, said two or more phenotypic Signed and Sealed this
Twenty-first Day of August, 2012

David J. Kappos
*Director of the United States Patent and Trademark Office*